United States Patent [19]

Yamagishi et al.

[11] Patent Number: 5,756,879
[45] Date of Patent: May 26, 1998

[54] VOLATILE ORGANIC COMPOUND SENSORS

[75] Inventors: Frederick G. Yamagishi, Newbury Park; Thomas B. Stanford, Oxnard; Camille I. van Ast, Newbury Park; Leroy J. Miller, West Hills, all of Calif.

[73] Assignee: Hughes Electronics, Los Angeles, Calif.

[21] Appl. No.: 685,997

[22] Filed: Jul. 25, 1996

[51] Int. Cl.⁶ .......................... G01N 27/00; G01N 07/00; C08F 283/00; B05D 5/12
[52] U.S. Cl. .................. 73/28.01; 73/23.31; 73/31.02; 204/424; 324/439; 324/691; 428/421; 422/90; 422/98
[58] Field of Search .................. 73/28.01, 24.04, 73/23.34, 23.31, 31.02, 31.03; 204/424; 324/439, 446, 691, 693; 428/421, 426; 422/90, 94, 98

[56] References Cited

U.S. PATENT DOCUMENTS

| | | | |
|---|---|---|---|
| 4,019,367 | 4/1977 | Norsworthy | 73/23 |
| 4,457,161 | 7/1984 | Iwanaga et al. | 73/23 |
| 4,674,320 | 6/1987 | Hirschfeld | 73/23 |
| 4,699,804 | 10/1987 | Miyata et al. | 437/176 |
| 4,721,601 | 1/1988 | Wrighton et al. | 422/68 |
| 4,822,465 | 4/1989 | Jones et al. | 204/192.1 |
| 4,907,441 | 3/1990 | Shurmer | 73/23 |
| 4,977,658 | 12/1990 | Awano et al. | 29/25.01 |
| 5,018,380 | 5/1991 | Zupancic et al. | 73/23.2 |
| 5,086,286 | 2/1992 | Yasukawa et al. | 338/34 |
| 5,208,301 | 5/1993 | Epstein et al. | 525/540 |
| 5,234,566 | 8/1993 | Osman et al. | 204/403 |
| 5,331,287 | 7/1994 | Yamagishi et al. | 324/724 |
| 5,337,018 | 8/1994 | Yamagishi et al. | 324/693 |
| 5,372,785 | 12/1994 | Johnson et al. | 422/90 |
| 5,407,699 | 4/1995 | Myers | 427/121 |
| 5,417,100 | 5/1995 | Miller et al. | 73/31.02 |
| 5,491,097 | 2/1996 | Ribi et al. | 436/518 |
| 5,520,852 | 5/1996 | Ikkala et al. | 252/521 |
| 5,536,473 | 7/1996 | Monkman et al. | 422/90 |
| 5,540,862 | 7/1996 | Cao et al. | 252/500 |
| 5,624,605 | 4/1997 | Cao et al. | 252/500 |
| 5,625,139 | 4/1997 | Stormbom | 73/23.21 |

FOREIGN PATENT DOCUMENTS 0 596 973 B1  12/1995  European Pat. Off. ....... G01N 27/12

OTHER PUBLICATIONS

M.D. Imisides et al, Chemtech, pp. 19–24 (May 1966).
E.W. Paul et al, Journal of Physical Chemistry, vol. 89, pp. 1441–1447 (1985).

*Primary Examiner*—Hezron E. Williams
*Assistant Examiner*—J. David Wiggins
*Attorney, Agent, or Firm*—V. D. Duraiswamy; W. K. Denson-Low

[57] ABSTRACT

A novel, inexpensive sensor and method for detecting volatile compounds in the gas phase at concentrations of less than about 500 ppm in ambient air are provided. The sensor comprises (a) a dielectric substrate having a major surface; (b) a pair of electrically conductive electrodes disposed on the major surface of the substrate; and (c) a conductive polymer covering the pair of electrically conductive electrodes, with the conductive polymer doped with appropriate dopants in measurable excess of that stoichiometrically required to change the conductive polymer from a neutral state to a charged state to provide requisite conductivity. A method for making the sensor is provided, as is a method of use of the sensor which relates to its use in a monitoring system comprising a means for measuring the conductivity of the sensor connected to a warning means for providing an indication when the conductivity reaches a predetermined level. Contemplated specific methods of use include the detection of fugitive emissions in chemical plant environments; the detection of certain pollutants in vehicle exhaust; and the detection of certain pollutants near chemical handling operations, such as painting operations.

44 Claims, 5 Drawing Sheets

VOLATILE ORGANIC COMPOUND SENSORS

This invention was made with Government support under Contract No. N00014-94-C-2278 awarded by the Department of the Navy and Cooperative Agreement No. N00014-95-2-0008. The Government has certain rights in this invention.

BACKGROUND OF THE INVENTION

1. Field of the Invention

The present invention relates generally to sensors for volatile compounds in the gas phase, and, more particularly, to highly sensitive sensors for sensing the presence of target volatile organic compounds contained in fugitive emissions and vehicle exhaust, among other applications.

2. Description of Related Art

There is an ever-increasing desire to reduce gaseous emissions from industrial sources, given the environmental and health threats such emissions may pose. Most of the industrial air pollutant emissions are generated by two types of companies, namely chemical manufacturing companies and oil refineries. Emissions from these types of industries are of two basic types: (1) stack gas emissions, and (2) fugitive emissions (i.e., leaks), the latter of which represent about one-half of the total emissions. Therefore, a major decrease in total emissions from these industrial sources will require a significant reduction of fugitive emissions.

There is a huge potential for the reduction of fugitive emissions in chemical plants and oil refineries. Both types of plants have processing facilities that are characterized by a large number of valves, flanges, and fittings, each of which is a potential source of fugitive emissions. A typical facility will have about 40,000 valves and about four to six times as many flanges, or about 100,000 to 300,000 potential leak sources. A leaker is typically defined as a fitting with 500 ppm or more hydrocarbon in the surrounding air, although some companies may employ a lower value.

Currently, personnel with sniffers walk through such facilities as chemical plants periodically checking for leaks. The hand-held sniffer typically consists of a long tube through which air samples are drawn to reach a flame ionization detector component. If there is a continuous problem with a valve or fitting, it is bagged and samples are taken for analysis by gas chromatography. High leakers, herein defined as those with 50,000 ppm or more of hydrocarbons in the surrounding atmosphere, must be identified quickly and repaired within 24 hours.

A primary problem with the use of sniffers for leak detection is that this method does not provide continuous, around-the-clock monitoring. Some fittings are checked as infrequently as once or twice a year. If a fitting leaks, the leak will continue until the next check period. Such un-repaired fittings may present an explosion hazard if allowed to leak undetected. Another problem with the use of sniffers is that there is often difficulty in reaching some valves for sampling, such as those near the ceiling or those on an offshore rig. Yet another problem in the use of sniffers by personnel is data management: each fitting must be recorded when it is checked.

Other areas in which the detection of volatile compounds in gaseous emissions would prove useful include the detection of pollutants (such as hydrocarbons, aromatics, and gaseous inorganic oxides) in vehicle exhaust and the detection of chemical weapon materials in military operations. These technologies would require sensors with increased sensitivities over those used to detect fugitive emissions. Specifically, sensors to be used in the ambient air in which target vapors are greatly diluted with air may require sensitivities of at least 100 ppm and often in the sub-ppm regime. In contrast, sensors for fugitive emissions can have relatively low sensitivity, since such sensors may be placed near the source of the leak or the leak can be partially confined in the region of the sensors such that the vapor concentration is very high. Thus, the detection of components in such applications as vehicle exhaust and military operations involving chemical weapons can be limited by the sensitivity of the sensors.

An inexpensive sensor that may be easily and flexibly employed in chemical plant environments to continuously monitor fugitive emissions is disclosed in U.S. Pat. No. 5,417,100, entitled "Reversible Sensor for Detecting Solvent Vapors" and assigned to the same assignee as the present application. Specifically, this patent discloses a fugitive emissions sensor for reversibly detecting solvent vapors that comprises a pair of electrically-conductive interdigitated electrodes disposed on the surface of a dielectric substrate and a composite coating covering the initerdigitated electrodes comprising (1) a conductive polymer having a conductivity within the range of about $10^{-6}$ to 1 S/cm, and (2) a dielectric polymer with an affinity for the solvent vapors of interest. The dielectric polymer is the major component of the composite coating and serves as an attractant for the targeted solvent vapor. The ratio of conductive polymer to dielectric polymer in the '100 patent is about 1:1 to 1:5. It is contemplated in the '100 patent that readings from such sensors as disclosed therein would be monitored and recorded by a computer, which would then notify operators of the occurrence and location of any detected leaks.

It is known to use conductive polymers as the active material in sensors for detecting a variety of compounds, such as acids, alcohols, complex metal ions, and proteins (see, e.g., M. D. Imisides et al, "Microsensors based on conducting polymers", *Chemtech*, May 1996, pp. 19–24). Stable conductive polymers include polypyrrole, polythiophene, and polyaniline (PANi); such materials may be readily modified by the attachment of particular functional groups and/or the incorporation of appropriate counterions during synthesis in order to detect, by selective interaction, specific compounds. Conductive polymer sensors are advantageous because they are compact, simple, inexpensive, and easy to make.

While the sensors disclosed in U.S. Pat. No. 5,417,100 are effective in sensing targeted solvent vapors, the composite nature of the material coating the electrodes undesirably adds complexity to the manufacture of the sensor, such as the attainment of uniformity of distribution of the conductive polymer and the dielectric polymer in the composite coating.

Another monitoring device using conductive polymers is known which indicates the presence of acid. This device is disclosed in U.S. Pat. No. 5,331,287, entitled "Device and Method for Sensing Water and/or Acid in the Presence of Water in Non-Aqueous Media" and assigned to the same assignee as the present application. Specifically, a sensor is disclosed therein for monitoring the water and acid content that is particularly suited for monitoring the quality of nonaqueous fluids in equipment or vehicles. The sensor comprises an insulating substrate, interdigitated electrodes formed on the substrate, and a conductive polymer deposited over the interdigitated electrodes that bridges between adjacent digits thereof. The conductive polymer reversibly increases conductivity in measurable amounts with increasing acid and/or water content due to protonation by the acid or hydration by the water. While the sensors of the '287 patent are effective in the monitoring of water and acid, the conductive polymer is limited in application to monitoring compounds capable of protonating the polymer, such as water and acid. The sensors do not employ specific counterions to alter the charge balance in the conductive polymer.

U.S. Pat. No. 5,337,018, entitled "Electronic Sensor for Determining Alcohol Content of Fuels" and assigned to the same assignee as the present application, discloses a sensor useful in measuring the alcohol content of gasoline. The sensor comprises a substrate, at least two electrodes deposited on the substrate, and a conductive polymer coating and thereby shorting the electrodes. The conductive polymer has a resistance that changes as a function of alcohol concentration. This resistance is achieved by converting the conductive polymer to its oxidized state, which is accomplished during electrochemical deposition rather than with an extra "doping" step. Similar to the sensors of U.S. Pat. No. 5,331,287, the sensors of the '018 patent are limited in application to the determination of a specific class of compounds, in this case alcohols.

European Pat. Application 596,973, entitled "Device for Sensing Volatile Materials", discloses a device for sensing volatile material in the gas phase comprising a pair of electrical contacts with a semi-conductive polymer extending between the contacts. A charge balance in the polymers is achieved using counterions in a proportion of about one counterion to four monomer units. Typical polymers used include polypyrrole, poly-N-methylpyrrole, poly-3-methylthiophene, polyaniline, poly-5-carboxyindole, poly-3-methyl-phenylamine, polybithiophene, polythiophene, poly-3-thiopheneacetic acid, and polyfuran. Typical counterions that may be used to synthesize the polymers may be tetrafluoroborate, alkyl sulphonates, tetramethylamimonium chloride, chlorates, and perchlorates. The sensors of the '973 reference are used in the form of an array to develop a fingerprint of a particular "odor." Specifically, the '973 reference teaches the use of an array of eleven sensors to distinguish between different brands of lager beer and between two samples of the same beer that had been stored differently. However, this document fails to disclose the detection of any other volatile organic compounds; any specific volatile organic compounds; threshold limits of detection of any volatile material; or the influence of counterions on the sensitivity of their sensors to any volatile materials.

Thus, a need remains for a compact, low-cost, highly-sensitive sensor having a conductive polymer as the active element that is adaptable for a method of monitoring gaseous emissions in an ambient environment for a variety of specific target volatile compounds which may be greatly diluted by air.

SUMMARY OF THE INVENTION

In accordance with the present invention, a sensor is provided which is based on a conductive polymer as the active transducer to detect the presence of target volatile compounds in ambient air environments. The conductivity of the conductive polymer is modulated predictably and reversibly in the presence of certain volatile compounds, thereby enabling the detection of such compounds. Specifically, the sensor comprises:

(a) a dielectric substrate having a major surface;

(b) a pair of electrically conductive electrodes disposed on the major surface of the substrate; and (c) a conductive polymer covering the pair of electrically conductive electrodes, the conductive polymer doped with appropriate dopants, with the dopants present in the conductive polymer in measurable excess of that stoichiometrically required to change the conductive polymer from a neutral state to a charged state to provide requisite conductivity.

The present sensor is capable of detecting the presence of a target volatile material at a concentration of less than about 500 ppm. A method of detecting target volatile material at less than about 500 ppm is provided employing this sensor.

At the heart of the invention is the use of pure conductive polymers, as opposed to composite films such as employed in U.S. Pat. No. 5,417,100, doped with counterions selected to attract certain specific chemical classes of volatile compounds which may be similar in nature to the counterion. The sensitivity of the sensors is unexpectedly increased by the use of an excess (greater than stoichiometric amount) of the conjugate counterion where the stoichiometric amount is only that amount required to balance all charge on the conductive polymer. The sensors of the invention are capable of an unexpectedly high degree of sensitivity to challenge vapors, such that these sensors are capable of detecting target vapors present at less than about 500 ppm in the surrounding ambient environment. A method of making the present sensors is provided which recites doping the conductive polymer with a stoichiometric excess of counterion to achieve enhanced sensitivity.

The sensor device of the invention is useful in the detection of target volatile compounds in ambient air environments. A method for using such a sensor device comprises (a) connecting the sensor to a mechanism capable of communicating the presence of the target volatile material upon detection thereof by the sensor; and (b) positioning the sensor such that it is exposed to ambient air in an area of concern regarding the presence of the target volatile material. Specific applications include the detection of fugitive emissions from fittings in chemical manufacturing environments; the detection of certain pollutants in vehicle exhaust; and the detection of certain pollutants near chemical handling operations, such as painting. It is contemplated that the sensors of the invention may be employed either independently or as part of an array of sensors. Specifically, a monitoring system might include a compilation of a number of sensors into an array, which, through appropriate data manipulation, would generate a signature for each vapor, even in the presence of other interferences. In this manner, one enhances the selectivity of the present sensors in operation while also reaping the benefit of their inherent sensitivity.

DESCRIPTION OF THE PREFERRED EMBODIMENTS

The sensor and method of the invention provide an easily implemented manner by which to monitor ambient air for the presence of certain target volatile compounds, such as polar and nonpolar volatile organic compounds and solvents. Specifically, this invention addresses polar compounds such as diethyl phosphite, dimethyl sulfoxide, methanol, triethyl phosphate, n-butyl acetate, and methyl isoamyl ketone, and non-polar compounds such as benzene, toluene, and xylene. The sensor is highly sensitive and is capable of detecting the presence of target volatile compounds to concentrations less than about 500 ppm in ambient air, or even less than about 100 ppm given the performance of certain steps in formulating the sensor.

Figure 1:
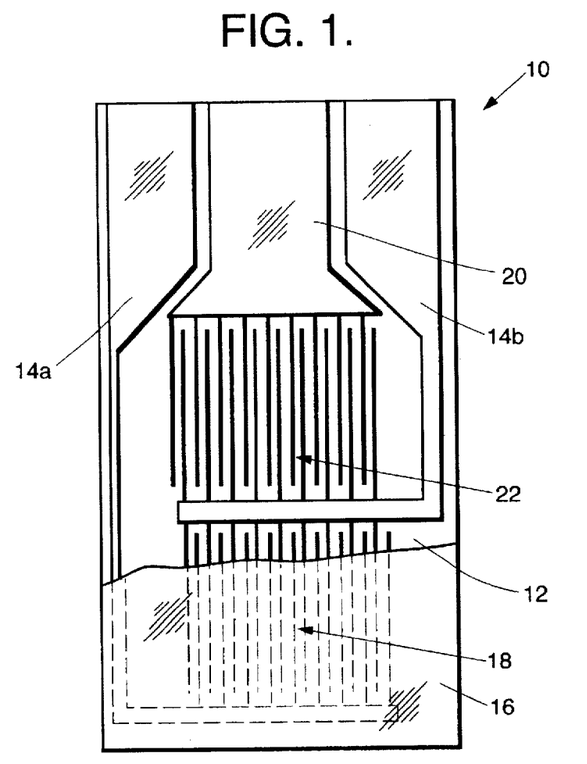
FIG. 1 is a top plan view of an interdigitated sensor of the invention.

FIG. 1 depicts an embodiment of the sensor 10 of the invention. The sensor 10 comprises (1) a dielectric substrate 12; (2) at least two electrically conductive electrodes 14a, 14b disposed on the surface of the substrate; and (3) a conductive polymer 16 having an affinity for the vapors that one wishes to detect. One electrode 14a is called the analyte electrode while the second electrode 14b is called the reference electrode. The conductive polymer 16 exists as a thin film coating the electrodes 14a, 14b. In FIG. 1, the polymer coating is broken away to show the underlying electrodes, which are interdigitated in this embodiment.

Examples of suitable dielectric substrates 12 include glass and ceramics. In this connection, any of the common silica-based, phosphate-based, borate-based or other oxide-based glasses or mixtures of these may be employed in the practice of the invention. Further, any of the common oxide ceramics, such as alumina, magnesia, calcia, quartz, and the like and mixtures of these may be employed in the practice of the invention. Alternatively, any dielectric polymer having a low affinity for hydrocarbon vapors may be employed in the practice of the invention. Examples of such dielectric polymers include polyethylene terephthalate, fluorinated polymers (such as Teflon™), the acrylics, such as poly (methyl methacrylate), and polyimides, such as Kapton™, which is commercially available from Du Pont of Wilmington, Del.

The electrically-conductive electrodes 14a, 14b generally comprise a conductive metal or metals, and preferably comprise metals that have no reactivity with the other components of the sensor or with the vapors present in the surrounding atmosphere. An example of a metal that has been successfully used for the electrodes 14a, 14b is gold, which has been formed over a tungsten-titanium alloy, the alloy serving to provide good adhesion of the gold to a glass substrate 12. Other suitable conductive materials include platinum, palladium, and carbon. As with gold, an adhesion layer, employing any of the well-known adhesion layer materials, may be employed in conjunction with the metal electrodes 14a, 14b. Preferably, the electrodes 14a, 14b comprise gold in the practice of the invention. The thickness of such adhesion layers is typically on the order of tens of Ångstroms.

The electrodes 14a, 14b may be arranged in an interdigitated fashion, as shown in FIG. 1, or may be in some other configuration, so long as the conductive polymer coating shorts the two electrodes. The electrode material is deposited on the insulating substrate by well-known deposition techniques, typically photolithographic techniques, and such process does not form a part of this invention. Typically, the metal layer is blanket-deposited and patterned.

The parameters of the interdigitation (ie., number of finger pairs, length of fingers, width of fingers, periodicity, and electrode thickness) are not critical. For exemplary purposes only, gold interdigitation may comprise 50 finger pairs, with each finger about 5 mm long, 25 µm wide, with a 60 µm period, and about 2 µm thick.

The use of two interdigitated electrodes 14a, 14b as shown in FIG. 1 provides an analyte area 18. The ambient air interacts with the conductive polymer 16 to change its conductivity if the target volatile compound is present in the air at detectable levels.

The electrical modulation in conducting polymers is sensitive to temperature, and it may be desirable to provide a means for compensating for operation of the sensor at higher temperature. One way to achieve this is to provide a third reference electrode 20. This reference electrode may be interdigitated with the reference electrode 14b to provide a reference area 22. The reference area, which is also covered with the conductive polymer 16, is further covered with an impervious material (not shown) so as to prevent interaction of the ambient air with the electrodes 14b, 20 in the reference area 22. Examples of suitable impervious materials include silicon dioxide, silicon nitride, poly(methyl methacrylate) polystyrene and multilayers derived therefrom. Both electrode areas 18 and 22 experience the same temperature, but only analyte area 18 reacts to the mixture containing the targeted volatile compound.

A conductive polymer suitably employed in the practice of the invention preferably is one having a conductivity of about $10^{-6}$ to 1 S/cm. However, it is not the absolute conductivity that is as important in the practice of the invention as is the change in conductivity as the sensor experiences different environments. Such change in conductivity is measured by a change in current, which can range as small as about 100 nA to about 100 mA. Such changes in conductivity can range from less than 1% to several orders of magnitude. Even small changes can be detected and therefore these changes in the conductivity of the conductive polymer 16 are readily correlated to the presence of the target volatile organic compound.

Examples of conductive polymers 16 suitably employed in the practice of the invention include polyaniline, polythiophene, polypyrrole, poly(p-phenylene vinylene), derivatives of these polymers, and mixtures of these materials. Examples of derivatives of the conductive polymers suitably employed in the practice of the invention are those with substituents on the aromatic rings. These substituents include alkyl groups (e.g., $C_4$ to $C_{18}$) and alkoxy groups (e.g., $OC_4$ to $OC_{18}$). The advantage of the longer chain alkyl and alkoxy groups is that the resulting polymers become more soluble the longer the chain, which is useful in casting thin films of the polymer. Preferably, polyaniline and polythiophene, and their derivatives, are employed in the practice of the invention, although polypyrrole and some of its derivatives also serve as good conductive polymer sensors.

The heart of this invention is the use of specifically-formulated conductive polymer films which are designed to provide highly sensitive volatile organic compound detection. It is believed that only certain sensor film formulations can provide the required sensitivity typically desired for volatile organic compound sensing applications, namely a sensitivity in the range of less than about 500 ppm.

The conductive polymers have an affinity for target vapors that may derive from the counterion associated with a conductive polymer. The conductive polymers 16 are typically doped with appropriate counterions to provide the polymers with the requisite conductivity—without doping, the polymers are always less conductive and may in fact be insulators.

Examples of counterions that may be suitably employed to serve as attractants in the conductive form of polyaniline include p-toluenesulfonate, copper phthalocyaninetetrasulfonate, poly(styrenesulfonate), camphorsulfonate, dodecylbenzenesulfonate, butanesulfonate, octanesulfonate, hexadecanesulfonate, octadecanesulfonate, and bisulfate. An example of a counterion suitably employed for the conductive form of polythiophene (and its 3-alkyl derivatives) is $FeCl_4$. Mixtures of counterions may be employed in the practice of the invention.

For polar volatile organic compounds such as triethyl phosphate, the proper choice of counterion in the conductive polymer is critical to sensitivity for such vapors. The counterions may be introduced into the polymer during the electrochemical preparation of the polymer, such as described in U.S. Pat. No. 5,417,100, among other techniques. Regardless of the manner of doping employed, the proper choice of counterion is essential in achieving high sensitivity to target vapors. Polyaniline conductive polymers containing copper phthalocyaninetetrasulfonate or toluenesulfonate demonstrate enhanced sensitivity over bisulfate or camphorsulfonate formulations. These materials afford an affinity for polar target vapor because of specific chemical interactions between the counterion and the vapor, thereby enhancing the sensitivity of their films for such polar vapors.

For non-polar volatile organic compounds such as toluene, low level sensitivity is also enhanced by counterion selection. Counterions such as dodecylbenzenesulfonate, octadecylsulfonate, and hexadecylsulfonate ions are suitable for detecting non-polar volatile organic compounds at or below about 500 ppm. Furthermore, in order to achieve a sensitivity on the order of less than about 100 ppm, the conductive polymer on the coated sensor must exist in a certain state. To achieve a sensitivity of less than about 100 ppm, the following four steps in preparing the sensor must be controlled through particular techniques:

1. the substrate surface is "pre-treated";
2. the polymer is prepared;
3. the polymer film is cast on the substrate surface; and
4. the sensor film is "post-treated" after preparation.

The particular steps necessary to achieve a sensitivity of less than about 100 ppm are discussed below. Suffice it to say that the extent to which each of these factors is important for sensor performance depends upon the conductive polymer used and the target vapor being sensed, and various combinations of techniques may be necessary for a given sensing task. Alternately, by using variations of these procedures, a wide variety of sensing elements may be prepared, providing differing response characteristics to a selected target vapor. Such an approach will be highly suitable for an array-based vapor selectivity and discrimination.

Conductive polymers such as polyaniline combined with counterions such as dodecylbenzenesulfonate, octadecylsulfonate, and hexadecylsulfonate ions are suitable for detecting non-polar volatile organic compounds at or below about 500 ppm, but for different reasons than for polar materials. These counterions certainly show a degree of affinity for the target vapors. However, counterion derived from surfactant sulfonic acids are preferred over other counterions such as bisulfate, camphorsulfonate, or toluenesulfonate, because the surfactant counterions also act as solubilizing agents for the conductive polymer. The effect of these counterions is to provide for a conformation of the conductive polymer which is more open and less tightly configured, resulting in a more conductive film and, most importantly, in a material having a conductivity that is more responsive to the presence of target organic vapors. It follows that, in the case of non-polar volatile organic compounds, the mechanism by which the polymer responds to the presence of the target vapor is enhanced, rather than the interaction of the polymer with the vapor.

It has been determined that an increase in sensor sensitivity (i.e., the ability to detect materials at concentrations of less than about 500 ppm) may be achieved by employing excess counterion in the preparation of the conductive polymer film such that both bound and unbound counterion is present in the film coating. Specifically, an increased sensitivity was demonstrated in the evaluation of polyaniline-dodecylbenzenesulfonate (DBSA) film. The additional unbound counterion serves to increase the extent of de-coiling of the polyaniline polymer and also the responsiveness of the polymer to organic vapors. The Examples below demonstrate that an excess of one part of DBSA added to one part of the conductive polymer complex substantially enhances sensor performance. This ratio is defined as "one part excess" as used below.

Besides introducing counterions into the polymer during electrochemical preparation of the polymer, the doping process may be accomplished by reacting the chemically-prepared polymer with an appropriate oxidizing agent. The latter process may result in a reduction of the oxidizing agent to an anionic moiety, which then serves as the counterion, or a counterion may be another anion in the solution.

The amount of dopant stoichiometrically required to provide the requisite conductivity is about 0.5 mole per mole of polymer. Less dopant results in reduced yield of the oxidized monomers, while more dopant will have one of the following three effects: (1) no effect, except that there would be an excess of dopant which would then be removed during reaction work-up; (2) attainment of the wrong polymer than desired (e.g., over-doped); and (3) over-oxidation causing decomposition. Once the conductive polymer is initially doped to the requisite conductivity, the counterion can be changed by simple ion exchange by exposing the original polymer to a solution of the desired new counterion which is present in huge excess. Preferably, to realize the benefits from employing excess counterion, which can range from 0.1 to 10 parts of the conjugate counterion to one part of the complexed conductive polymer, is exposed to one part of a conjugate counterion.

The conductive polymers may also have an affinity for target vapors in their insulating state. i.e., without being doped with counterions as described above. Rather, certain polymers may have an affinity for target vapors deriving from the alkyl or alkoxy substituents attached to the polymer or from the chemical nature of the polymer itself. Therefore, it is contemplated that certain so-called "conductive" polymers might actually be employed in sensors for target vapors while remaining in their less conductive or "insulating" state.

The manner of depositing the conductive polymer film 16 onto the electrodes 14a, 14b may be accomplished by any conventional means. This process does not form part of the invention. However, it is noted that casting the films onto the electrodes can result in insufficient adhesion for practical application, but under certain casting conditions, this method can become useful. Depositing the conductive polymer thin film 16 electrochemically results in uniform thin films with strong adhesion. Another advantage of this deposition method is that the resulting polymer film is oxidized in situ so that conductive material is obtained directly, and the extra doping step may be eliminated. Such electrochemical deposition is well-known in the art.

It is therefore typical to connect adjacent electrode surfaces 14a, 14b in parallel and to grow the conductive polymer 16 in solution, with the lateral propagation of the conductive polymer bridging the gap between electrodes. Thus, the conductive polymer 16 is deposited on the substrate 12 over the electrodes 14a,14b as a thin film. Preferably, the electrode region is completely covered.

The thickness of the polymer coating 16 must be sufficient to cover the gap between the electrodes 14a,14b, but not so thick as to crack. Coatings on the order of 25 μm are considered to be preferred in this application, although the thickness may vary from about 0.1 to 50μm, depending upon the size of the gap.

Figure 2:
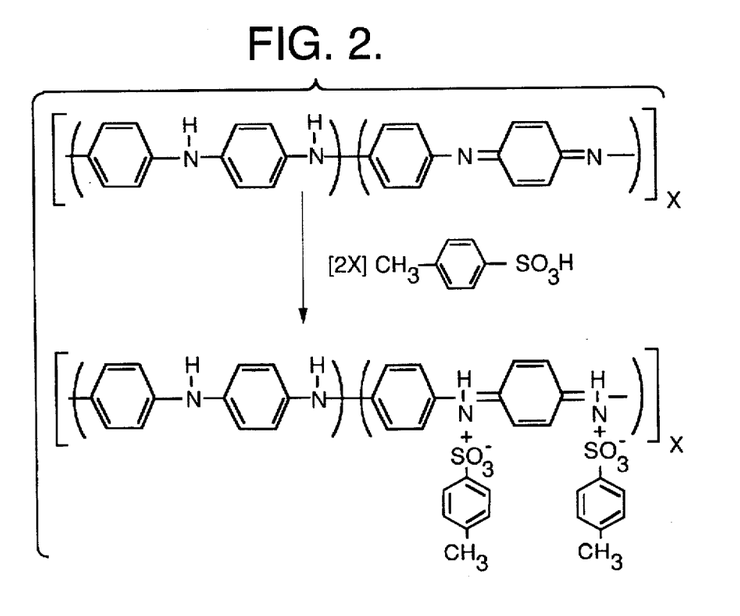
FIG. 2 depicts the chemical structure of the insulating emeraldine base form and the conductive emeraldine salt form of polyaniline, shown as the p-toluenesulfonic acid salt, which is employed as a conductive polymer in the practice of the invention.

The present invention preferably employs polyaniline as the conductive polymer 16. Derivatives of polyaniline, such as alkyl- or alkoxy-substituted polyanilines may be used as well. FIG. 2 illustrates the emeraldine base or insulating form of polyaniline which is then protonated by p-toluenesulfonic acid to the conductive form. Polyaniline is a long chain, highly conjugated material. Microscopically, polyaniline forms a highly fibrous morphology. The fibers are generally highly intertwined to yield a macroscopic material resembling a sponge with a high surface area. It is the exposure of the high surface area of polyaniline to the surrounding ambient air that renders polyaniline so sensitive to the presence of a target volatile compound.

Moreover, the thermal stability of polyaniline is good. The neutral material shows stability up to 420° C., and the doped or protonated material can show stability up to 250° C., but is somewhat dependent on the chemical structure of the associated anion.

The source of the conductivity in a conductive polymer is electronic not ionic. In other words, the movement of charge through the film is advantageously accomplished by the movement of electrons, not by the migration of ions, as provided in conventional electrochemical devices which measure the concentration of ions present in a medium. Removing the sensor from the presence of the vapor being detected and placing it in uncontaminated ambient air allows the absorbed species to desorb and results in return of the sensor to its original conductivity. Thus, the sensor of the invention may be generally cycled repeatedly in detecting a given species.

In general terms, while a sensor may detect a given species in a matter of seconds or minutes, the amount of time required for the sensor to recover its original conductivity by exposure to uncontaminated-ambient air is measured in terms of hours or days, since the desorption process is a function of several factors such as boiling point of the adsorbed species and the ambient temperature. Thus, the time required for the sensor to recover original conductivity dominates the sensor's total cycle time. However, the sensor of the invention evidences partial recovery of its original conductivity as quickly as one minute after being placed in uncontaminated ambient air. The below-reported examples illustrate these time-related features of the invention.

In order to further improve sensor sensitivity such that materials are detectable at concentrations of less than about 100 ppm as opposed to 500 ppm, certain other steps in the process of making the sensor should be performed in addition to employing excess counterion. Specifically, these steps regard the concentration and dispersion characteristics of the organic solution employed to spin the conductive polymer as well as the energy state of the substrate surface. Each of these factors are discussed below in seriatim.

With regard to the concentration of the spinning solution, polymer films such as polyaniline-DBSA will provide significantly enhanced responsiveness to non-polar volatile organic compound vapors when prepared by spinning from dilute organic solutions, meaning solutions having concentrations of about 10% or less. Spinning in this manner results in the rapid formation of a polymer film onto the sensor substrate surfaces in a manner such that coiling of the polymer chains is minimized. This technique of film deposition provides for an open polymer configuration and further enhances the ability of the film to respond to low levels of volatile organic compounds.

With regard to the dispersive characteristics of the spinning solution, it is important that the solution from which such films are prepared be free of agglomerated polymer material, thereby minimizing coiled chain configuration in the prepared film. The solution from which a polymer film is cast must be dilute and thoroughly treated prior to film deposition with such methods as ultrasonication to prevent and eliminate agglomeration and association of polymer chains in the prepared film.

Furthermore, it is also determined that the substrate surface upon which the conductive film is placed must be suitably deactivated to allow the response behavior required for sensitivity below 100 ppm. Glass and gold substrate surfaces are relatively high energy hydrophilic surfaces and as such will influence the conformation of conductive polymer films placed thereon. When used in the hydrophilic state, these surfaces tend to cause reduced polymer response to volatile organic compound vapors. If such surfaces are properly treated to enhance their hydrophobicity, they become suitable for enhancing the vapor response characteristics and the resulting polymer films become appropriately responsive for detecting low level volatile organic compounds. Surface treatments such as silation with typical silane coupling agents, such as hexamethyldisilazane, or N-phenylaminopropyltrimetlhoxysilane, octyltrichlorosilane, octyltrimethoxysilane, octadecyltrichlorosilane, or octadecyltrimethoxysilane are applied to clean substrate samples using common vapor treatment techniques, prior to applying polymer films such as polyaniline-DBSA as discussed above. As much as a 200-fold increase in responsiveness has been observed for polyaniline-DBSA films when placed on substrate surfaces in this manner.

To illustrate the sensitivity of the present sensor 10, it has been demonstrated that the sensor can detect the presence of xylene in ambient air at concentrations as low as 440 ppm (see Examples below). The EPA estimates that typical fugitive emissions from leaking valves is 5.6 g/hr and from leaking flanges is 0.83 g/br. A leak of 100 µL (about 0.065 g) or more per hour could easily be programmed to set off an alarm to notify the operator. To do this, the sensor could be confined inside a plastic (e.g., Mylar™) wrapping around the potential leak source. A small opening would be provided to keep the internal and external pressures equal. The sensitivity will depend on the internal volume of the wrapped space, and on the size of the opening to the external environment.

Figure 3:
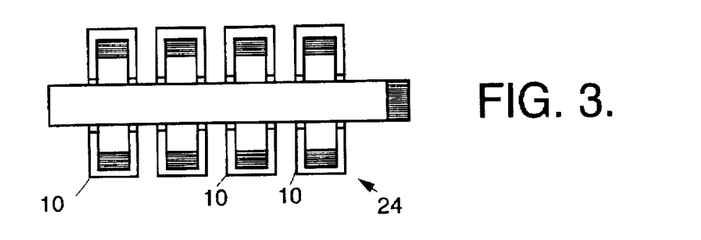
FIG. 3 is a schematic showing implementation of the sensor of the invention as part of an array of sensors.

In practice, an array 24 of sensor devices such as depicted in FIG. 3 may be employed which comprises individual sensor devices 10 each capable of detecting a specific compound but which, as a whole, provides a characteristic pattern of responses (or "finger-print") to a particular target material or "odor". The use of arrays 24 of sensor devices 10 to fingerprint target odors is known (see, e.g., M. D. Imisides et al., *Id.* at page 24). Such arrays 24 are advantageous because they may be employed to effectively monitor target vapors even in the presence of relatively major interferences.

Figure 4:
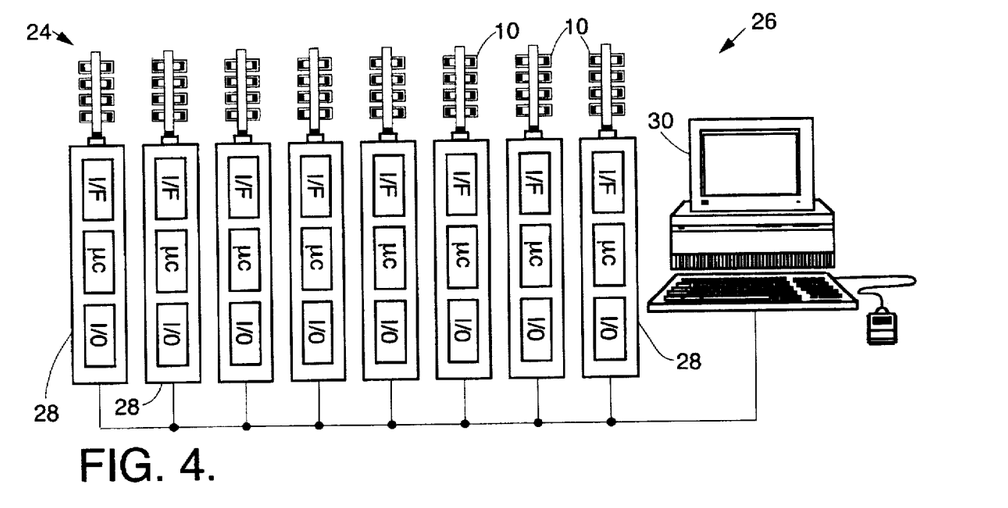
FIG. 4 is a schematic showing implementation of the sensor of the invention in an alarm system.

It is contemplated that the present sensors will be incorporated into monitoring systems 26 as illustrated in FIG. 4. The presence of the target species in ambient air surrounding the sensor 10 will cause a change in conductivity in the sensor of the invention. The signal caused by the change in conductivity can be monitored through wiring to an ammeter 28 and subsequently read by a computer 30. Alternatively, the electrical signals from the sensor can be converted to optical pulses which can be detected by an appropriate detector (e.g., a photodiode) (not shown) or transmitted through fiber optic lines (not shown), then converted to electrical signals at the ammeter. Another alternative would be that the response of the sensor be converted to pulses in the radio frequency range which would be transmitted in space without the need for wires. These pulses would be collected by an antenna (not shown) and converted to electrical signals at the ammeter 28. The computer 30 may be programmed with an algorithm to detect threshold current values that would define a leak, for example, along with time constants and other pertinent variables, such as temperature. Correlation of these parameters will determine a point at which an "alarm" should be turned on. The alarm could be in the form of an audible tone (e.g., bell, siren, etc.), a flashing light, or combination thereof.

Thus, while the sensor 10 could be operated independently, the sensors of the invention may also be employed as part of a monitoring system 26 in which a computer 30 monitors a network of sensors. It is noted that the power source for sensor operation is not limited but may comprise any known means for energy supply, such as hard wiring for electrical service, a solar cell, or battery operation. The power requirements for running the sensor are very low, on the order of about 10 nW to 10 mW per sensor. The sensor operates at ambient temperature, so there is no danger of causing an explosion associated with the use of the present sensors.

In the temperature-compensated system, the conductivity between the two analyte electrodes 14a, 14b and between the two reference electrodes 14b, 20 is determined. This measurement is again accomplished by conventional means, and does not form a part of this invention. The resulting signal is then further processed to accurately determine whether the target volatile compound is present in the sampled ambient air.

The cost of these sensors would be very low. Improvements in design may also be envisioned that would allow the electrodes and the conductive polymer film to be "printed" on a plastic backing. The sensor could be stapled to the wrapping, and the staples could also be the leads to the electrodes. The following examples are provided to illustrate the preparation and properties of the sensor of the invention.

EXAMPLES

Figure 5:
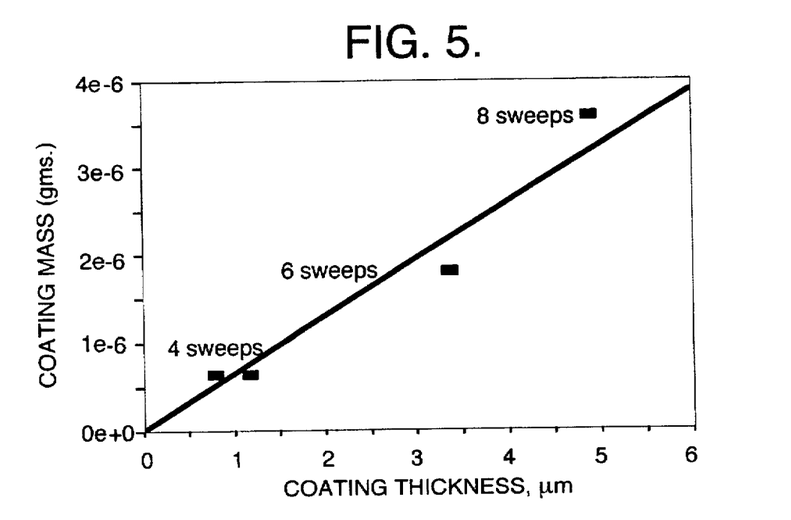
FIG. 5, on coordinates of coating mass (in grams) versus coating thickness (in µm), is a plot of coating mass as a function of coating thickness for different deposition sweeps.

A thin film of polyaniline was deposited over gold interdigitated electrodes on a glass slide. The electrodes consisted of 50 finger or digit pairs, each 5 mm long and 25 µm wide, with a 60 µm period, 2 µm thick. The gold electrodes were sputter-deposited over a thin layer of sputter-deposited tungsten-titanium alloy, about 25 to 100 Å thick, employing photolithography to define the interdigitated electrodes. The polyaniline was prepared and deposited by well-known electrochemical methods starting with an aqueous solution containing sulfuiric acid, sodium hydrogen sulfate, and freshly distilled aniline (in solution as the anilinium salt), as described by Paul, et al., *J Phys. Chem.* Vol. 89, 1441 (1985). The polyaniline was electrochemically prepared with a BAS-100B Electrochemical Analyzer operating in the cyclic voltammetry mode between 0 and 900 mV DC with a sweep rate of 50 mV/sec in a two-compartment cell with the interdigitated electrode as the cathode. All potentials were measured against a standard saturated calomel electrode, with a platinum mesh counterelectrode. The number of cycles employed depended upon the desired thickness and oxidation state of the film so produced. It was empirically determined that thickness in the electrochemically-prepared films is controlled by the reaction conditions and the number of layers that are deposited under those conditions. The general procedure employed in the fabrication of the film is described in detail below:

1. Prepared 25 mls solution in water comprising:
   a. 1.1M conductive polymer (e.g., aniline)
   b. 1.1M counterion/electrolyte (e.g., 0.5M $H_2SO_4$/0.6M $NaHSO_4$)
2. Electropolymerized as follows:
   a. Swept from 0 to 900 mV ( 50 mV/sec, sweeping four times using monomer (e.g., aniline) only;
   b. Rinsed with deionized water;
   c. Swept from 0 to 450 mV ( 50 mV/sec, sweeping one time using a solution of organic counterion or copolymer; and
   d. Rinsed with deionized water The thickness of polyaniline coatings applied to sensors were measured by a stylus method (Dektak Model 3030 Surface Profile Measuring System) for sensors prepared with different numbers of sweeps in the monomer solution (see FIG. 5.)

Furthermore, by appropriately choosing the parameters of the last sweep, the oxidation state of the produced film is established as either fully reduced, half-oxidized, or fully oxidized. In the example represented by FIG. 5, the final sweep of 0–450 mV established an oxidation state of half-oxidized for the formed film. The polyaniline was therefore converted to the emeraldine base form for the practice of the invention (meaning equal units of oxidized and reduced states). Polyaniline, prepared in this manner, was also protonated or doped by the respective counterion in solution during electrochemical preparation. In the above example, polyaniline doped with bisulfate (i.e., $HSO_4$) was produced. By substituting 1.1M toluenesulfonic acid or copper phthalocyaninetetrasulfonate solutions for 0.5M $H_2SO_4$/0.6M $NaHSO_4$, doping with these counterions was accomplished. Polyaniline, prepared in this manner, was deposited on the substrate over the interdigitated electrodes and was grown between the electrodes to completely bridge between adjacent digits. Detection sensitivities were initially screened by connecting leads to the sensor element and applying a dc voltage of about 0.2 V between the electrodes and monitoring the resulting current as the sensor element was exposed to a challenge vapor—the current was about 0.2 two 5.0 mA. Upon exposure the resistivity of the transducer changed, which was then manifested in a modulation of the current. Each prepared sensor element was exposed to saturated vapor at room temperature in the head-space of a small jar containing several milliliters of the challenge vapor. The saturated room temperature concentration levels of typical representative polar and non-polar vapors are reported below in Table 1:

TABLE 1

Calculated concentrations resulting from static saturated vapor challenges

| Vapor | Concentration (parts per thousand) |
|---|---|
| Hexane | 157.6 |
| Toluene | 28.6 |
| Diethyl phosphite | 3.30 |
| Dimethyl sulfoxide | 0.56 |
| Methanol | 126.8 |

Alternatively, screening was done in some cases in a closed static system composed of a 600 ml vessel which contained the sensor element at room temperature. Measured amounts of the challenge liquid was introduced into the vessel through a syringe after which the liquid vaporized into the much larger volume. Liquid volumes of 2 µL amounted to 1,300 (octane) to 2,600 (thiophene) ppm. Data (electrical current vs. time) were collected either manually or by computer and were later analyzed.

Figure 6:
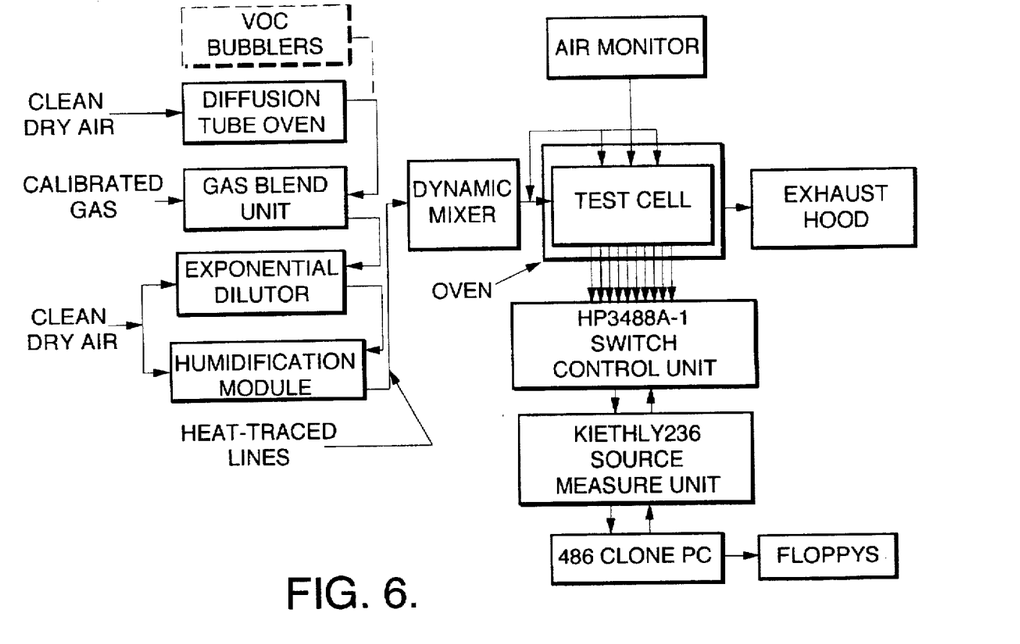
FIG. 6 is a schematic of a typical test apparatus employed in performing the examples described below.

Alternatively, a special test station was employed that used permeation tubes at constant temperature and constant humidity. Data was collected by computer using a data logging application (LabVIEW, National Instruments). A scanner was used to address each sensor individually during the test at appropriate intervals so that data from each sensor could be collected at once. FIG. 6 is a detailed schematic of this test apparatus.

Following collection of the data it was plotted as sensor response (current) vs. time. It was observed that it was difficult to compare the raw data from sensors that were nominally identical. However plotting normalized sensor response vs. dosage (concentration×time) generally yielded a straight line whose slope was defined as a figure of merit (FOM) and could be used to compare various sensors. The absolute magnitude of the slope was a function of the response time of the sensor and was indicative of the sensitivity of the sensor to a particular challenge vapor. Table 2 reports the ranking of various polyaniline-based sensors with various counterions and thicknesses according to the FOM:

TABLE 2

Sensitivities of polyaniline-based sensors as a function of counterion (TSA = p-toluenesulfonate, CuPc = copper phthalocyaninetetrasulfonate) and thickness to triethyl phosphate, sorted by figure of merit.

| SENSOR NO. | COUNTERION | POLYMER THICKNESS, µM | CHALLENGE VAPOR CONC, PPM | FOM × $10^4$ | FOM CORRELATION COEFFICIENT |
|---|---|---|---|---|---|
| 51-83 | TSA | 3.2 | 12.1 | 2.80 | 0.999 |
| 51-71 | TSA | 10.4 | 12.1 | 2.20 | 0.998 |
| 51-70 | TSA | 10.4 | 12.1 | 2.08 | 0.998 |
| 52-35 | CuPc | 2.0 | 12.1 | 2.02 | 0.995 |
| 51-69 | TSA | 10.4 | 12.1 | 1.85 | 0.986 |
| 52-31 | CuPc | 4.4 | 12.1 | 1.81 | 0.995 |
| 52-26 | CuPc | 10.0 | 12.1 | 1.79 | 0.993 |
| 51-67 | TSA | 4.0 | 12.1 | 1.73 | 0.993 |
| 51-66 | TSA | 4.0 | 12.1 | 1.57 | 0.994 |
| 51-81 | TSA | 3.2 | 12.1 | 1.37 | 0.994 |
| 51-68 | TSA | 4.0 | 12.1 | 1.22 | 0.995 |
| 51-82 | TSA | 3.2 | 12.1 | 0.87 | 0.996 |
| 52-12 | CuPc | 2.0 | 50.0 | 0.47 | 0.990 |
| 52-11 | CuPc | 2.0 | 50.0 | 0.39 | 0.989 |
| 51-10 | CuPc | 10.0 | 50.0 | 0.36 | 0.986 |
| 51-25 | TSA | 4.0 | 50.0 | 0.12 | 0.962 |
| 51-28 | TSA | 10.4 | 50.0 | 0.11 | 0.983 |
| 51-29 | TSA | 10.4 | 50.0 | 0.09 | 0.983 |
| 51-26 | TSA | 4.0 | 50.0 | 0.08 | 0.981 |
| 51-24 | TSA | 4.0 | 50.0 | 0.08 | 0.977 |
| 51-27 | TSA | 10.4 | 50.0 | 0.07 | 0.975 |
| 51-32 | TSA | 2.0 | 50.0 | 0.06 | 0.977 |
| 51-31 | TSA | 2.0 | 50.0 | 0.05 | 0.971 |
| 51-30 | TSA | 2.0 | 50.0 | 0.04 | 0.969 |

Figure 7:
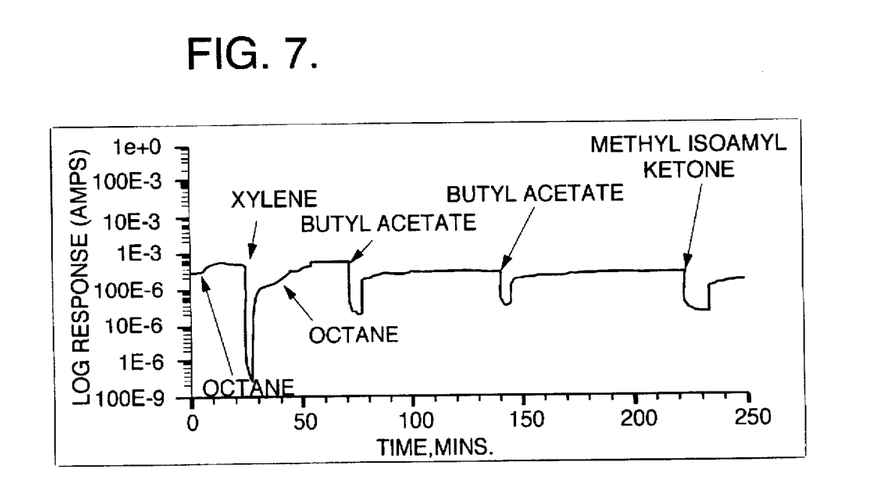
FIG. 7, on coordinates of sensor current (in amps) versus time (in minutes), is a plot of current as a function of time employing one embodiment of the device of the invention in response to various challenged vapors, namely octane, xylene, butyl acetate, and methyl isoamyl ketone.

Sensor elements composed of polyaniline doped with dodecylbenzenesulfonic acid (Pani—DBSA) or camphorsulfonic acid (PANi-CSA) showed sensitivity to a number of classes of room temperature saturated challenge vapors, especially aromatic hydrocarbons, as shown in FIG. 7. Pani—DBSA and PANi-CSA samples were prepared from 1% solutions of the material supplied by Uniax (Uniax Company, Santa Barbara, Calif.) in either chloroform or xylene solutions containing a one part excess of the respective counterion. Preparation of these solutions required stepwise addition of the polymer (about 25% of the total per step) in a 1% solution of the respective counterion in the respective solvent, with sonication of 2 to 3 hours between each addition, followed by a final sonication of about 8 hours. All sensors were prepared immediately before testing using freshly filtered solutions which were spin-coated at 2,000 rpm for 20 seconds. After spinning, samples were then placed in a vacuum desiccator for about one hour before testing. Table 3 below shows relative response data for several conductive coatings and demonstrates the performance enhancements afforded by the considerations discussed above. The polyaniline—DBSA spin-coated samples, which contained a one part excess of DBSA, gave significantly greater response to saturated toluene vapor than the other counterion formulations or preparation methods.

TABLE 3

Response Data with 2,800 ppm Toluene Vapor (1.1 pm flow at 20% RH)

| Sample | Response, delta |
|---|---|
| PHT*/DBSA/CHCl$_3$ (90-2) cast | −0.006 |
| PHT/DBSA/CHCl$_3$ (90-3) cast | −0.004 |
| PHT/DBSA/CHCl$_3$ (90-4) + PANi-DBSA overcoat | −0.003 |
| PANi-DBSA (55389-1) electrochem. | −0.005 |
| PANi-DBSA (55389-2) electrochem. | −0.01 |
| PHT/CHCl$_3$ (83-13) | −0.0006 |
| PHT/CHCl$_3$ (83-14) + PANi-DBSA overcoat | −0.005 |
| PHT/CHCl$_3$ (83-18) | 0.006** |
| PANi-DBSA (55375-5/3), excess DBSA spin-coated | −0.021 |
| PANi-DBSA (55375-5/4), excess DBSA spin-coated | −0.022 |
| PANi-DBSA (55375-5/5), excess DBSA spin-coated | −0.015 |
| PANi-DBSA (55375-5/6), excess DBSA spin-coated | −0.02 |

Notes:
*Poly(3-hexylthiophene)
**Positive Response
numbers in parentheses are sample numbers The response value in the right hand column of Table 3 is defined as:

delta=(response−baseline)/baseline, where
- baseline=current reading 2 to 5 minutes after "zero" (i.e., the time when challenge is turned off or zero air) and
- response=current reading 1 to 2 minutes before "zero".

Figure 8:
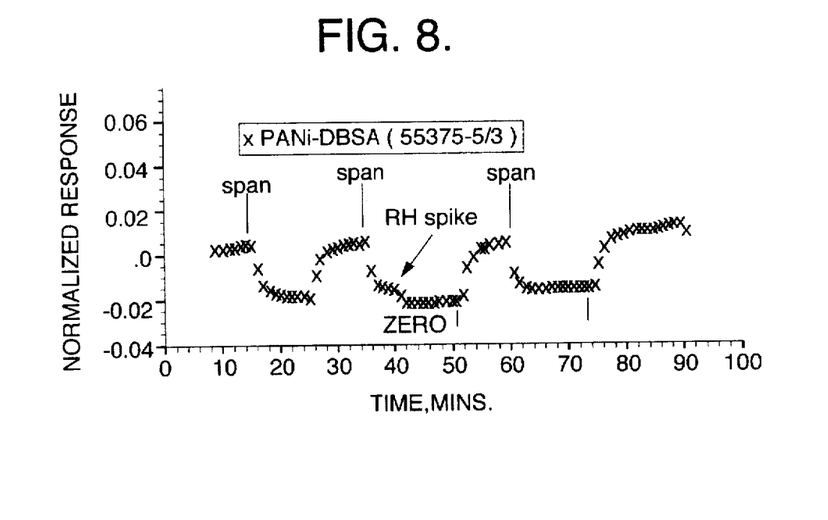
FIG. 8, on coordinates of normalized response versus time (in minutes), depicts the response curve obtained for a polyaniline-dodecylbenzenesulfonate sensor versus toluene.

FIG. 8 shows a response curve obtained for such a polyaniline—DBSA sample containing a one part excess of DBSA. In particular, FIG. 8 represents the response of the polyaniline—DBSA sample from Table 3 above having a delta value of −0.021.

Figure 9:
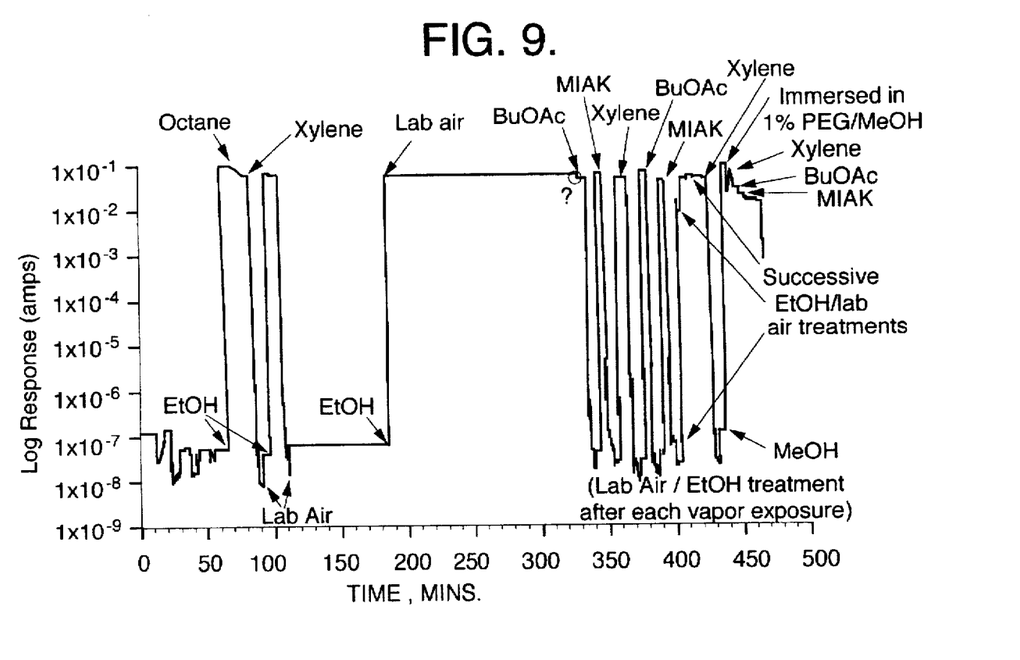
FIG. 9, on coordinates of sensor current (in amps) versus time (in minutes), is a plot of current as a function of time employing a sensor using Monsanto's soluble solyaniline, which is doped with a proprietary counterion, in response to various challenge vapors, including octane, xylene, butyl acetate, methyl isoamyl ketone, and also in response to immersion in a solution of polyethylene glycol and methanol.

A sensor element was similarly tested prepared from a sample of Monsanto's Soluble Polyaniline (Monsanto Co., St. Louis, Mon.) which is doped with dinonylnaphthalene-sulfonic acid. This material is provided by the supplier as a solution containing about 61% polymer, in 2:1 xylene/Butyl Cellosolve. Sensor samples of this material were prepared as described above. Although it showed responses to room temperature saturated vapors, the response for such samples was significantly less than that shown by polyaniline doped with dodecylbenzenesulfonic acid. However, the sensitivities were tremendously increased if the Monsanto material was exposed to ethanol (to which the sensor was extremely sensitive) prior to exposure to the other challenge vapors. This "preconditioning" appears to be a reorganization of the film's morphology into one that is more susceptible to interaction with the challenge vapors. These results are illustrated in FIG. 9.

Figure 10:
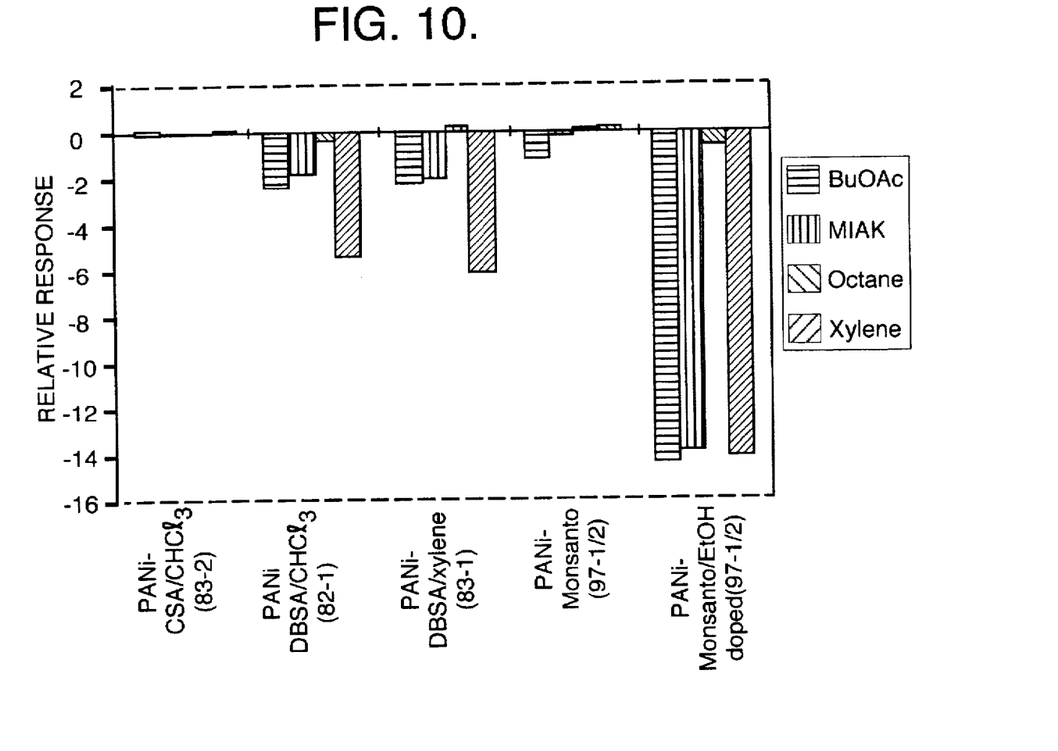
FIG. 10 is a bar graph depicting, for various compositions of sensor coatings, the relative responses to butyl acetate, methyl isoamyl ketone, octane, and xylene.

FIG. 10 shows a comparison of the relative sensitivity to saturated vapor concentrations of butyl acetate (BuOAc), methyl isoamyl ketone (MIAK), octane, and xylene for polyaniline films with various counterions. These results demonstrate the greatly enhanced response realized with DBSA v. CSA and dinonylnaphthalenesulfonate (Monsanto Co.) counterions. Also shown in FIG. 10 is a polyaniline dinonylnaphthalenesulfonate film which was treated with an alcohol solvent (ie., designated as doped with EtOH, where EtOH means ethanol), apparently resulting in a similar uncoiling phenomena within this film sample and giving rise to a material with greatly enhanced sensitivity to each vapor tested.

Figure 11:
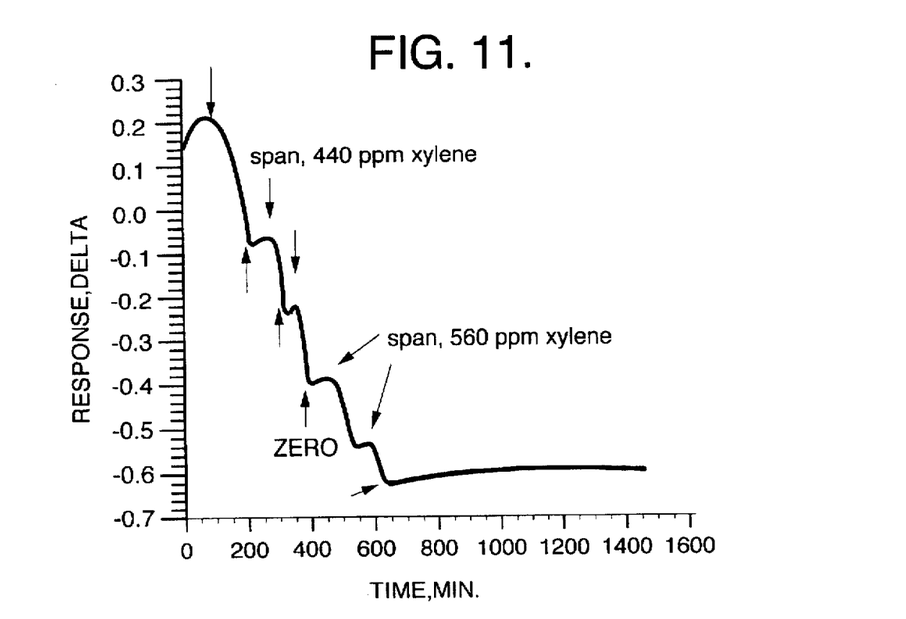
FIG. 11, on coordinates of normalized response versus time (in minutes), depicts the response curve obtained for a polyaniline-dodecylbenzenesulfonate sensor versus toluene, with the conductive polymer coating of the sensor containing an excess dodecylbenzenesulfonate in the practice of the invention.

Further studies with vapor challenges below 500 ppm demonstrate response values (delta) of greater than −0.001 for xylene, toluene, MIAK, and BuOAc at comparable exposure periods. These data indicate sufficient sensitivity to these vapors for this sensor such that a delta obtained from 100 ppm or less (assuming linear behavior) can be easily detected. The response curves shown in FIG. 11 are representative of such results. Using Pani—DBSA samples prepared as described above (one part excess DBSA), tests were conducted at 1.0 liter/minute flow and 20% RH with a xylene concentration of 440 and 560 ppm. These results show a response change of over −0.1 delta units with a 440 ppm xylene exposure of about 60 minutes.

Sensor elements prepared by casting or spinning from solutions of regioregular poly(3-alkylthiophene-2, 5-diyl) (available from Rieke Metals, Inc., Lincoln, Neb.), where the alkyl group consisted of hexyl, octyl, decyl, or dodecyl, were found to be sensitive to hexane, toluene, chloroform, methylene chloride, octane, diethyl ether, and acetone. It was essentially insensitive to ethanol, methanol, and water. Generally the change in response of the sensor was about 15% or less, but methylene chloride gave changes in response as high as a factor of about 20.

Sensor substrate surfaces may be treated to enhance the responsiveness of the films cast thereon. Surface treatments with the silating agents N-phenylaminopropyl trimethoxysilane were performed to clean substrate samples using common vapor treatment techniques, prior to applying a polyaniline—DBSA film as discussed above.

As much as a 200-fold increase in responsiveness to saturated toluene vapor has been observed for polyaniline—DBSA films when placed on substrate surfaces prepared in this manner.

INDUSTRIAL APPLICABILITY

The sensor and methods of the invention are expected to find use in detecting leaks in the fittings and valves of petroleum refineries and chemical manufacturing and processing plants, as well as to detect gaseous pollutants from vehicle exhaust and from remediation sites in remote areas.

Thus, there has been disclosed a sensor and method for reversibly detecting volatile material in the gas phase as well as a method of making and using such a sensor and a monitoring system employing an array of such sensors. It will be readily apparent to those skilled in the art that various changes and modifications of an obvious nature may be made without departing from the spirit of the invention, and all such changes and modifications are considered to fall within the scope of the invention as defined by the appended claims.

What is claimed is:

1. The invention claimed is a sensor for reversibly detecting target volatile material in the gas phase comprising:

(a) a dielectric substrate having a major surface;

(b) a pair of electrically conductive electrodes disposed on said major surface of said substrate; and (c) a conductive polymer covering said pair of electrically conductive electrodes, said conductive polymer doped with appropriate dopants, said dopants present in said conductive polymer in measurable excess of that stoichiometrically required to change said conductive polymer from a neutral state to a charged state to provide requisite conductivity, said sensor being capable of detecting the presence of said target volatile material at a concentration of less than about 500 ppm.

17 wherein said dielectric substrate is deactivated by a surface treatment means that enhances the hydrophobicity of surface on said substrate.

2. The invention claimed is the sensor of claim 1 wherein said conductive polymer is prepared by spin-casting from dilute organic solutions having a concentration of less than about 10% and wherein said dilute organic solutions are substantially free of agglomeration.

3. The invention claimed is the sensor of claim 2 wherein said sensor is capable of detecting the presence of said target volatile material at a concentration of less than about 1 00 ppm.

4. The invention claimed is the sensor of claim 1 wherein said electrically conductive electrodes comprise a material selected from the group consisting of gold, platinum, palladium, and carbon.

5. The invention claimed is the sensor of claim 4 wherein said electrically conductive electrodes consist essentially of gold.

6. The invention claimed is the sensor of claim 5 wherein said gold electrodes are formed on an adhering layer that adheres said gold electrodes to said substrate.

7. The invention claimed is the sensor of claim 1 wherein said conductive polymer is selected from the group consisting of polyaniline, polythiophene, polypyrrole, poly(p-phenylene vinylene), derivatives of these polymers, and mixtures of these materials.

8. The invention claimed is the sensor of claim 7 wherein conductive polymer is polyaniline and said dopants are selected from the group consisting of p-toluenesulfonate, copper phthalocyanine-tetrasulfonate, poly (styrenesulfonate), camphorsulfonate, dodecylbenzenesulfonate, butanesulfonate, octanesulfonate, hexadecanesulfonate, octadecanesulfonate, and bisulfate.

9. The invention claimed is the sensor of claim 1 wherein said measurable excess is about one part over that stoichiometrically required to change one part of said conductive polymer from a neutral state to a charged state to provide requisite conductivity.

10. The invention claimed is the sensor of claim 1 wherein said dielectric substrate comprises a material selected from the group consisting of glass, ceramics and dielectric polymers.

11. The invention claimed is the sensor of claim 10 wherein said dielectric substrate comprises a glass selected from the group consisting of silica, phosphate, and borate glasses and mixtures thereof.

12. The invention claimed is the sensor of claim 10 wherein said dielectric substrate comprises a ceramic selected from the group consisting of alumina, magnesia, calcia, quartz, and mixtures thereof.

13. The invention claimed is the sensor of claim 10 wherein said dielectric substrate comprises a dielectric polymer selected from the group consisting of polyethylene terephthalate, poly(tetrafluoroethylene), poly(methyl methacrylate), and polyimides.

14. The invention claimed is a method of making a sensor for reversibly detecting target volatile material in the gas phase comprising:

(a) providing a dielectric substrate having a major surface;

(b) disposing a pair of electrically conductive electrodes on said major surface of said substrate; and (c) preparing a conductive polymer for disposition on said electrically conductive electrodes by doping said conductive polymer with an excess of appropriate dopants, said dopants present in said conductive polymer in measurable excess of that stoichiometrically required

18 to change said conductive polymer from a neutral state to a charged state to provide requisite conductivity; and (d) covering said pair of electrically conductive electrodes with said doped conductive polymer, said sensor being capable of detecting the presence of said target volatile material at a concentration of less than about 500 ppm, further comprising step (a',) following step (a):

(a') deactivating said dielectric substrate by a surface treatment means that enhances the hydrophobicity of surface on said substrate.

15. The invention claimed is the method of claim 14 wherein said dielectric substrate is deactivated by silation with a silating agent selected from the group consisting of hexamethyidisilazane, N-phenylaminopropyltrimethoxysilane, octyltrishlorosilane, octyltrimethoxysilane, octadecyltrichlorosilane and octadecyltrimethoxysilane.

16. The invention claimed is the method of claim 14 wherein said electrically conductive electrodes comprise a material selected from the group consisting of gold, platinum, palladium, and carbon.

17. The invention claimed is the method of claim 14 wherein said dielectric substrate comprises a material selected from the group consisting of glass, ceramics, and dielectric polymers.

18. The invention claimed is a method of making a sensor for reversibly detecting target volatile material in the gas phase comprising:

(a) providing a dielectric substrate having a major surface;

(b) disposing a pair of electrically conductive electrodes on said major surface of said substrate; and (c) preparing a conductive polymer for disposition on said electrically conductive electrodes by doping said conductive polymer with an excess of appropriate dopants, said dopants present in said conductive polymer in measurable excess of that stoichiometrically required to change said conductive polymer from a neutral state to a charged state to provide requisite conductivity; and (d) covering said pair of electrically conductive electrodes with said doped conductive polymer.

said sensor being capable of detecting the presence of said target volatile material at a concentration of less than about 500 ppm.

wherein said electrically conductive electrodes comprise a material selected from the group consisting of gold, platinum, palladium and carbon, and wherein said electrically conductive electrodes consist essentially of gold and wherein said method further comprises a step (a") immediately prior to step (b):

(a") depositing an adhering layer on said dielectric substrate comprising a tungsten—titanium alloy.

19. The invention claimed is the method of claim 14 wherein said conductive polymer is selected from the group consisting of polyaniline, polythiophene, polypyrrole, poly (p-phenylene vinylene), derivatives of these polymers, and mixtures of these materials.

20. The invention claimed is the method of claim 19 wherein said conductive polymer is polyaniline and said dopants are selected from the group consisting of p-toluenesulfonate, copper phthalocyaninetetrasulfonate, poly(styrenesulfonate), camphorsulfonate, dodecylbenzenesulfonate, butanesulfonate, octanesulfonate, hexadecanesulfonate, octadecanesulfonate, and bisulfate.

21. The invention claimed is the method of claim 14 wherein step (c) further comprises spin-casting said conductive polymer from a dilute organic solution having a concentration of less than about 10%.

22. The invention claimed is the method of claim 21 wherein step (c) further comprises minimizing agglomeration in said dilute organic solution.

23. The invention claimed is the method of claim 22 wherein said agglomeration is minimized by ultrasonication.

24. The invention claimed is the method of claim 22 wherein said sensor is capable of detecting the presence of said target volatile material at a concentration of less than about 100 ppm.

25. The invention claimed is the method of claim 14 wherein said measurable excess is about one part over that stoichiometrically required to change one part of said conductive polymer from a neutral state to a charged state to provide requisite conductivity.

26. The invention claimed is the method of claim 14 further comprising step (d):

(d) drying said doped conductive polymer prior to exposing said sensor to said target volatile material.

27. The invention claimed is a method of detecting a target volatile material in ambient air, said method comprising the steps of:

(a) providing a sensor comprising:
  (i) a dielectric substrate having a major surface;
  (ii) a pair of electrically conductive electrodes disposed on said major surface of said substrate, and
  (iii) a conductive polymer covering said pair of electrically conductive electrodes, said conductive polymer doped with appropriate dopants, said dopants present in said conductive polymer in measurable excess of that stoichiometrically required to change said conductive polymer from a neutral state to a charged state to provide requisite conductivity, said conductive polymer having a conductivity that changes as a function of the presence of said target volatile material, said sensor being capable of detecting the presence of said target volatile material at a concentration of less than about 500 ppm;

(b) exposing said sensor to ambient air to generate a signal that is a function of said conductivity; and (c) monitoring said conductivity of said conductive polymer, said method resulting in the detection of said target volatile material at a concentration of less than about 500 ppm.

wherein said dielectric substrate comprises a material selected from the group consisting of glass, ceramics, and dielectric polymers, and wherein said dielectric substrate is deactivated by a surface treatment means that enhances the hydrophobicity of surface on said substrate.

28. The invention claimed is the method of claim 27 wherein said conductive polymer is prepared by spin-casting from dilute organic solutions having a concentration of less than about 10% and wherein said dilute organic solutions are substantially free of agglomeration.

29. The invention claimed is the method of claim 28 wherein said sensor is capable of detecting the presence of said volatile material at a concentration of less than about 100 ppm.

30. The invention claimed is the method of claim 27 wherein said electrically conductive electrodes comprise a material selected from the group consisting of gold, platinum, palladium, and carbon.

31. The invention claimed is the method of claim 30 wherein said electrically conductive electrodes consist essentially of gold.

32. The invention claimed is the method of claim 31 wherein said gold electrodes are formed on an adhering layer that adheres said gold electrodes to said substrate.

33. The invention claimed is the method of claim 27 wherein said conductive polymer is selected from the group consisting of polyaniline, polythiophene, polypyrrole, poly (p-phenylene vinylene), derivatives of these polymers, and mixtures of these materials.

34. The invention claimed is the method of claim 27 wherein said conductive polymer is polyaniline and said dopants are selected from the group consisting of p-toluenesulfonate, copper phthalocyaninetetrasulfonate, poly(styrenesulfonate), camphorsulfonate, dodecylbenzenesulfonate, butanesulfonate, octanesulfonate, hexadecanesulfonate, octadecanesulfonate, and bisulfate.

35. The invention claimed is the method of claim 27 wherein said measurable excess is about one part over that stoichiometrically required to change one part of said conductive polymer from a neutral state to a charged state to provide requisite conductivity.

36. The invention claimed is the method of claim 27 wherein said step of exposing comprises placing said sensor in the vicinity of an area of concern regarding the presence of said target volatile material.

37. The invention claimed is the method of claim 27 wherein said step of monitoring comprises measuring the conductivity between said electrodes.

38. The invention claimed is a method of using a sensor for reversibly detecting a target volatile material in the gas phase comprising a dielectric substrate having a major surface: a pair of electrically conductive electrodes disposed on said major surface of said substrate; and a coating covering said pair of electrically conductive electrodes, said coating consisting essentially of at least one conductive polymer doped to achieve a requisite conductivity and to have an affinity for said target volatile material, said method comprising the steps of:

(a) connecting said sensor to a mechanism capable of communicating the presence of said target volatile material upon detection thereof by said sensor; and (b) positioning said sensor such that said sensor is exposed to ambient air in an area of concern regarding the presence of said target volatile material.

wherein said target volatile material is chemical weapon simulant material and said area of concern is selected from the group consisting of the vicinity of a potential chemical weapon deployment and the vicinity of chemical weapon manufacture.

39. The invention claimed is the method of claim 38 wherein said area of concern is in the vicinity of human handling of a material potentially containing said target volatile material.

40. The invention claimed is the method of claim 38 wherein said at least one conductive polymer is doped with appropriate dopants, said dopants present in said at least one conductive polymer in measurable excess of that stoichiometrically required to change said at least one conductive polymer from a neutral state to a charged state to provide requisite conductivity, said at least one conductive polymer having a conductivity that changes as a function of the presence of said target volatile material, said sensor being capable of detecting the presence of said target volatile material at a concentration of less than about 500 ppm.

41. The invention claimed is a method of using a sensor for reversibly detecting a target volatile material in the gas phase comprising a dielectric substrate having a major surface; a pair of electrically conductive electrodes disposed on said major surface of said substrate; and a coating covering said pair of electrically conductive electrodes, said coating consisting essentially of at least one conductive polymer doped to achieve a requisite conductivity and to have an affinity for said target volatile material said method comprising the steps of:

(a) connecting said sensor to a mechanism capable of communicating the presence of said target volatile material upon detection thereof by said sensor; and (b) positioning said sensor such that said sensor is exposed to ambient air in an area of concern regarding the presence of said target volatile material, wherein said dielectric substrate is deactivated by a surface treatment means that enhances the hydrophobicity of surface on said substrate, wherein said conductive polymer is prepared by spin-casting from dilute organic solutions having a concentration of less than about 10%, and wherein said dilute organic solutions are substantially free of agglomeration, said sensor being capable of detecting the presence of said target volatile material at a concentration of less than about 100 ppm.

42. The invention claimed is a monitoring system for monitoring the content of a target volatile material in ambient air, said monitoring system, comprising:

(a) at least one sensor for reversibly detecting said target volatile material in the gas phase, said at least one sensor positioned to be exposed to said ambient air, said at least one sensor comprising;

(i) a dielectric substrate having a major surface;

(ii) a pair of electrically conductive electrodes disposed on said major surface of said substrate; and (iii) a conductive polymer covering said pair of electrically conductive electrodes, said conductive polymer doped with appropriate dopants, said dopants present in said conductive polymer in measurable excess of that stoichiometrically required to change said conductive polymer from a neutral state to a charged state to provide requisite conductivity, said conductive polymer having a conductivity that changes as a function of the presence of said target volatile material, said sensor being capable of detecting the presence of said target volatile material at a concentration of less than about 500 ppm, wherein said dielectric substrate is deactivated by a surface treatment means that enhances the hydrophobicity of surface on said substrate;

(b) a conductivity detector for measuring the conductivity of the sensor, said conductivity detector being capable of indicating when said conductivity reaches a predetermined level;

(c) an alarm for providing an indication when said predetermined level is reached; and (d) interconnectors for interconnecting said sensor and said alarm to said conductivity detector.

43. The invention claimed is the monitoring system of claim 42 wherein said at least one sensor comprises an array of sensors.

44. The invention claimed is the monitoring system of claim 42 wherein said at least one sensor is capable of detecting the presence of said target volatile material at a concentration of less than about 100 ppm.

* * * * *

UNITED STATES PATENT AND TRADEMARK OFFICE
CERTIFICATE OF CORRECTION

PATENT NO. : 5,756,879  Page 1 of 2
DATED : May 26, 1998
INVENTOR(S) : Frederick G. Yamagishi, et al.

It is certified that error appears in the above-identified patent and that said Letters Patent is hereby corrected as shown below:

On the title page: Item [56], add the following,

U. S. PATENT DOCUMENTS

| EXAMINER INITIAL | | PATENT NUMBER | | | | | | ISSUE DATE | PATENTEE | CLASS | SUBCLASS | FILING DATE IF APPROPRIATE |
|---|---|---|---|---|---|---|---|---|---|---|---|---|
| | | 5 | 3 | 3 | 7 | 0 | 1 | 8 | 08/09/94 | Yamagishi, et al. | | | |
| | | 5 | 4 | 1 | 7 | 1 | 0 | 0 | 05/23/95 | Miller, et al. | | | |
| | | 4 | 6 | 2 | 4 | 7 | 5 | 6 | 11/25/86 | Matsuda, et al. | | | |
| | | | | | | | | | | | | | |

UNITED STATES PATENT AND TRADEMARK OFFICE
CERTIFICATE OF CORRECTION

PATENT NO. : 5,756,879
DATED : May 26, 1998
INVENTOR(S) : Frederick G. Yamagishi, et al.

It is certified that error appears in the above-identified patent and that said Letters Patent is hereby corrected as shown below:

FOREIGN PATENT DOCUMENTS

| | | DOCUMENT NUMBER | | | | | | PUBLICATION DATE | COUNTRY OR PATENT OFFICE | CLASS | SUBCLASS | TRANSLATION YES | NO |
|---|---|---|---|---|---|---|---|---|---|---|---|---|---|
| | | WO | 95/ | 3 | 2 | 4 | 2 | 2 | 11/30/95 | McNeight, et al. | | | | |
| | | | | | | | | | | | | | | |

OTHER DOCUMENTS

| | | |
|---|---|---|
| | Temofonte, T. et al. "Phthalocyanine sensors for room-temperature ppb level detection | |
| | of toxic gases" Journal of Applied Physics Volume 65, Number 03, New York, N.Y. | |
| | USA. (01 February 1989) | |

Signed and Sealed this

Fourth Day of May, 1999

Attest:

Attesting Officer

Q. TODD DICKINSON

Acting Commissioner of Patents and Trademarks